United States Patent [19]

Traitler et al.

[11] Patent Number: 5,243,046
[45] Date of Patent: * Sep. 7, 1993

[54] PROCESS FOR THE CONTINUOUS FRACTIONATION OF A MIXTURE OF FATTY ACIDS

[75] Inventors: Helmut Traitler, Vevey; Hans-Juergen Wille, Clarens, both of Switzerland

[73] Assignee: Nestec S.A., Vevey, Switzerland

[*] Notice: The portion of the term of this patent subsequent to Apr. 21, 2009 has been disclaimed.

[21] Appl. No.: 836,793

[22] Filed: Feb. 14, 1992

Related U.S. Application Data

[63] Continuation of Ser. No. 127,781, Dec. 2, 1987, Pat. No. 5,106,542.

Foreign Application Priority Data

Dec. 17, 1986 [CH] Switzerland ............... 05027/86

[51] Int. Cl.⁵ .............................. C11C 1/08
[52] U.S. Cl. ........................ 554/186; 554/175
[58] Field of Search .................... 554/186, 175

[56] References Cited

U.S. PATENT DOCUMENTS

| | | | |
|---|---|---|---|
| 2,520,716 | 8/1950 | Fetterly | 554/39 |
| 2,653,122 | 9/1953 | Arnold et al. | 208/25 |
| 2,717,890 | 9/1955 | Drechsel | 554/196 |
| 2,723,220 | 11/1955 | Axe | 208/25 |
| 2,750,361 | 6/1956 | Gorin et al. | 554/186 |
| 3,720,696 | 3/1972 | Osawa | 554/185 |
| 4,140,620 | 2/1979 | Paulett | 208/33 |
| 4,377,526 | 3/1983 | Fujita et al. | 554/185 |
| 4,541,917 | 9/1985 | West | 208/31 |
| 4,776,984 | 10/1988 | Traitler et al. | 554/157 |

FOREIGN PATENT DOCUMENTS 1240513 7/1971 United Kingdom .

OTHER PUBLICATIONS

Traitler, et al. Fraktionierung mehrfach ungesättigter Fettsäuren aus verschiedenen natürlichen Rohstoffen, Fette, Seifen, Anstrichmittel, vol. 88, No. 10(1986) pp. 378–382, and an English translation thereof.

Willi, et al., Kontinuierliches Verfahren zur Anreicherung von Mehrfach ungesättigten Fettsäuren, Fat. Sci. Technol., vol. 90, No. 12(1988), and an English Translation thereof.

McGraw-Hill Encyclopedia of Science & Technology 6th Edition, pp. 275,277 and 380–382 (1987).

Swern, et al. Application of Urea Complexes in the Purification of Fatty Acids, Esters and Alcohols.III. Concentrates of Natural Linoleic and Linolenic Acids. J. Am. Oil Chem. Soc., vol. 3, No. 1 (1955).

Primary Examiner—Patrick P. Garvin
Assistant Examiner—E. D. Irzinski
Attorney, Agent, or Firm—Vogt & O'Donnell

[57] ABSTRACT

A mixture of fatty acids, including derivatives thereof, containing polyunsaturated fatty acids, including derivatives thereof, are reacted with urea in solution. The reaction medium is pumped through at least one scraped-surface heat exchanger for cooling the reaction medium for forming a dispersion of a solid inclusion complex and a liquid phase. The liquid phase which contains a fraction enriched with polyunsaturated fatty acids, including derivatives thereof, then is separated from the inclusion complex.

15 Claims, No Drawings

PROCESS FOR THE CONTINUOUS FRACTIONATION OF A MIXTURE OF FATTY ACIDS

CROSS-REFERENCE TO RELATED APPLICATIONS

This is a continuation application of application Ser. No. 07/127,781 filed Dec. 2, 1987, now U.S. Pat. No. 5,106,542.

BACKGROUND OF THE INVENTION

This invention relates to the fractionation of a mixture of fatty acids to obtain a fraction enriched with biologically active polyunsaturated fatty acids.

It is known that fatty acids having different degrees of saturation can be separated from a mixture by formation of an inclusion complex with urea in the presence of a solvent and separation of the liquid fraction enriched with the complex. For example, French patent no. 1 603 383, which corresponds to British patent no. 1 240 513, relates to the enrichment with γ-linolenic acid (triunsaturated) of a mixture of fatty acids emanating from the oil of the evening primrose "Oenothera" which additionally contains fatty acids having a lower degree of unsaturation.

There are also known processes for the selective enrichment with polyunsaturated fatty acids, of which the first double bond is in the Δ6-position (for example γ-linolenic acid), of a mixture of fatty acids additionally containing polyunsaturated fatty acids, of which the first double bond is in the Δ9-position (for example α-linolenic acid), by complexing with urea under specific conditions which involves separation of the position isomers (see, for example, published European patent no. 178 442). Although this process, which is not continuous, leads to satisfactory enrichment from the point of view of selectivity and yield either on a laboratory scale or on a pilot scale, it is difficult to carry out on an industrial scale. For example, in batches of several t., the formation of the inclusion complex in a tank takes place very slowly. It only works properly, i.e., with acceptable selectivity, with very slow stirring. As a result, the heat exchanges are poor. Now, fine adjustment of the reaction temperature is necessary in order not to cause the redissolution and/or ageing of the urea crystals which would then no longer be capable of including the fatty acids, thereby giving rise to a reduction in the selectivity of enrichment.

SUMMARY OF THE INVENTION

The object of the present invention is to eliminate the above-mentioned disadvantages. The invention relates to a process for the continuous fractionation of a mixture of fatty acids or fatty acid derivatives containing polyunsaturated fatty acids or derivatives thereof in which the mixture is reacted with a complexing agent such as urea in solution in a reaction medium, the medium is cooled to form an inclusion complex insoluble in the medium, the inclusion complex formed is separated in solid form and a fraction enriched with polyunsaturated fatty acids or derivatives thereof is collected in the liquid phase, characterized in that the insoluble complex is formed by cooling of the reaction medium in one to five scraped-surface heat exchangers arranged in line.

DETAIL DESCRIPTION OF THE INVENTION

The starting material used may be a mixture of fatty acids or fatty acid derivatives emanating from a fat of vegetable or animal origin rich in polyunsaturated fatty acids. The vegetable fats used include oils rich in linoleic acid (diunsaturated), for example safflower oil, sunflower oil, grape seed oil, corn oil, soybean oil; oils rich in fatty acids having a higher degree of unsaturation, for example linseed oil, comfrey seed oil "*Symphytum officinale*", evening primrose seed oil "Oenothera", quandong seed oil "*Santalum acuminatum*", borage seed oil "*Borago officinalis*" or oil from the seeds of fruit of the genus "Ribes", for example blackcurrant "*Ribes nigrum*".

The animal fats used include fish oil, oil from crustaceans, oil from cephalopods and lipids emanating from the organs or body fluids of mammals. The fatty acids may be obtained from the above-mentioned lipids, for example by hydrolysis at high temperature and pressure or, preferably, by saponification. The saponification may be carried out from dried and ground seeds or pips, from dried seeds or pips converted into flakes, pellets or granules or even from the oil extracted from these seeds or pips. It may be carried out on lipids of animal origin in liquid form. These lipids may contain a considerable proportion of unsaponifiables which are advantageously separated.

The fatty acid derivatives mentioned are preferably the esters, for example the methyl esters obtained by reaction of triglycerides with sodium methylate. It is preferred to use the acids rather than their esters because the enrichment yield is better.

The saponification may be carried out in the usual way by treating the starting material with a concentrated strong base, for example sodium hydroxide, preferably in a hot aqueous or aqueous-alcoholic medium. This medium advantageously contains a sequestering agent for metallic ions, for example disodium ethylenediamine tetraacetate. The unsaponifiables are then separated using a solvent, for example hexane, and the aqueous phase is acidified, for example with hydrochloric acid in concentrated aqueous solution.

After saponification, the mixture obtained may be protected against oxidation by addition of an anti-oxidant, for example 100 to 600 ppm (parts per million) of propyl gallate or, preferably, 200 to 400 ppm of ascorbyl palmitate.

The soaps obtained during the neutralization of the crude oil while it is being refined may also be used as starting material.

The fractionation comprises working under conditions which promote the formation of a complex of the fatty acids with the complexing agent in a reaction medium in which the complexing agent is soluble, but the inclusion complexes formed are insoluble. Urea is preferably used as the complexing agent. The reaction medium may consist cf a good solvent for urea, for example a lower alkanol, i.e., an alkanol containing from 1 to 4 carbon atoms, preferably methanol, ethanol, isopropanol or a mixture of these alkanols with water. Methanol is particularly suitable, as is a solution containing approximately 85% by weight of methanol for approximately 15% by weight of water.

In a tank provided with means for stirring and for thermostatic control, for example by circulation of water in a double jacket, the preferably saturated solution, for example of urea in methanol, is prepared and the fatty acids added with vigorous stirring at 60°-65° C. until a clear solution is obtained. The ratio by weight of urea to solvent is 1:1.5 to 1:3 while the ratio by weight of fatty acids to urea is from 1:3 to 1:6 and preferably from 1:3 to 1:4.

The solution is then pumped through at least one and up to five scraped-surface heat exchangers arranged in line. Alternatively, it is possible for example to replace the scraped-surface heat exchanger at the end of the line by a dwell pipe provided with cooling means.

It is in this line that the insoluble complex is precipitated. The inflowing solution may be at the dissolution temperature, for example at 60°-65° C., or may even have been cooled, for example to 20°-40° C. The heat exchangers are cooled by a refrigerating liquid circulating at high speed, for example ice water, ethanol, freon, ammonia, of which the temperature is −25° to +5° C. and preferably from −16° to +2° C. The throughput of material depends on the cooling capacity of the heat exchangers and of the refrigerating fluid used. The rotational speed of the scraping elements may be as high as 3000 r.p.m. but is preferably between 500 and 1000 r.p.m. Thus, the total residence time in the line is a few seconds to a few minutes. The final temperature of the dispersion issuing from the last exchanger plays a decisive role in the separation of the solid and liquid phases. It is between −5° and 15° C., depending on the nature of the fatty acids to be fractionated.

After the treatment in the scraped-surface heat exchangers, the dispersion is advantageously directed to a tank cooled to approximately 2° C., after which the solid phase is separated from the liquid phase by filtration, preferably under a slight vacuum, or by centrifugation.

After elimination of the alkanol, for example by distillation in vacuo, the liquid phase is treated with an acid, for example concentrated hydrochloric acid, for acidification to a pH of approximately 1 to make the unreacted urea pass into aqueous solution, and a solvent, for example hexane, is added to extract the fatty acids, for example by decantation, recovery of the organic phase and elimination of the solvent, being for example by distillation in vacuo. For example, it is possible to collect the methanol and then the hexane which may be re-used.

Alternatively, it is possible to dispense with one or both of the steps of acidification and extraction with a solvent.

The solid phase still contains fatty acids which it may be desired to recover. To this end, water may be added to the complex, preferably in a ratio by weight of complex to water of approximately 1:2, followed by heating to the release the fatty acids which may then be extracted from the aqueous phase, for example with hexane. The hexane may be eliminated from this second organic phase and the fatty acids recovered may be combined with the starting fatty acids to be fractionated, thus increasing the yield.

So far as the urea is concerned, it may be used for example as fertilizer because it is no longer sufficiently active.

The crude fatty acid fractions obtained may advantageously be decolored, for example by treatment with 0.5 to 5% by weight of bleaching earths, preferably at a temperature of approximately 80° C. The optionally decolored fractions may then advantageously be purified, for example by distillation at 150° to 210° C. under a vacuum of 13 to 133 Pa (0.1 to 1 mmHg) in a countercurrent apparatus.

The optionally decolored and/or purified fatty acid fractions may be stabilized by protecting them against oxidation, for example by addition of approximately 200 ppm (parts per million) by weight of ascorbyl palmitate.

The fatty acid fractions obtained in accordance with the invention may be used in the usual applications of these acids either as such or in the form of the oil obtained by recombination with glycerol. Brought into a form suitable for their application, the fractions enriched with polyunsaturated fatty acids may constitute nutritive, cosmetic, dermatological or pharmaceutical products, as described for example in European patents 92 085 and 92 076. These products are suitable for oral, enteral, parental or topical administration.

The fatty acid fractions may also be used as starting material in the synthesis of rare fatty acids, for example dihomo-γ-linolenic acid from a fraction enriched with γ-linolenic acid in known manner, for example by the synthetic or enzymatic route.

EXAMPLES

The invention is illustrated by the following Examples in which parts and percentages are by weight, unless otherwise indicated.

EXAMPLE 1

In a double-jacketed tank, 213 kg of a solution containing 101.5 kg water, 30.6 kg sodium hydroxide, 80.6 kg ethanol and 0.3 kg disodium ethylenediamine tetraacetate are added with slow stirring to 100 kg of fully refined (decolored and purified) blackcurrant seed oil, after which the solution is heated for 30 minutes to 60° C. The solution is then cooled to 30° C. with 40 kg cold water and then acidified to pH 1 with 100 kg of a 32% aqueous hydrochloric acid solution which is added slowly. After addition of 167 kg hexane, the mixture is vigorously stirred for 1 h at 30° C. The phases are then left standing for 15 minutes to separate and the aqueous phase is eliminated. After evaporation of the hexane from the organic phase in a water pump vacuum at 40° C., 90 kg fatty acids are collected.

30 kg urea and 63 kg methanol are added to 10 kg of the fatty acids collected, followed by heating with vigorous stirring for 20-30 minutes at 65° C. until a clear solution is obtained.

The solution is then pumped through a scraped-surface heat exchanger of the KOMBINATOR type under the following conditions:

| Exit temperature: | 1° C. |
|---|---|
| Rotational speed of scrapers: | 500 r.p.m. |
| Throughput: | 35 kg/h |
| Refrigerating fluid, freon at: | −15° C. |

The dispersion issuing from the apparatus is directed to a double-jacketed tank cooled to 2° C. where it remains for 10 to 20 minutes. The dispersion is then filtered through a GAF bag filter.

The methanol is evaporated in a water pump vacuum at 40° C. and the liquid phase is taken up in 8 kg hexane, followed by the addition of 6.7 kg of a 32% aqueous hydrochloric acid solution to a pH value of 1 and 18 kg water.

The phases are then left standing to separate, the organic phase is collected and 8 kg hexane are added to the aqueous phase. After stirring, the organic phase is collected and combined with the preceding organic phase, after which the hexane is evaporated at 40° C. in a water pump vacuum.

The percentages of γ-linolenic acids, $C_{18}$: 3, 6, 9, 12 (GLA) in the starting oil and in the enriched fraction (as determined by gas chromatography) are shown below:

|  | GLA (%) |
|---|---|
| Blackcurrant seed oil | 17.4 |
| Enriched fraction | 65 |

EXAMPLES 2-7

The procedure is as in Example 1, except that the solution containing the fatty acids, the urea and the methanol is passed through a line comprising in series: a first scraped-surface heat exchanger of the VOTATOR type (exchanger 1), a second scraped-surface heat exchanger of the VOTATOR type (exchanger 2) and a pipe (exchanger 3) cooled with ice water to 1° C.

The data concerning the starting material, the treatment conditions and the enriched fraction are shown in Table 1 below (the percentages of GLA are determined by gas chromatography):

TABLE 1

| Examples starting material (S.M.) | % GLA in S.M. | Throughput (kg/h) | Exchanger 1 Entry T. (°C.) | Exchanger 1 Exit T. (°C.) | Rotational speed of scraper (r.p.m.) |
|---|---|---|---|---|---|
| 2. Fatty acids of blackcurrant seed oil | 17.4 | 21.6 | 63 | 30.1 | 500 |
| 3. Fatty acids of blackcurrant seed oil | 17.4 | 21 | 28 | 18.3 | 500 |
| 4. Fatty acids of comfrey seed oil | 26.9 | 20 | 31 | 16.5 | 500 |
| 5. Fatty acids of borage seed oil | 24.7 | 40 | 65 | 19 | 700 |
| 6. Fatty acids of evening primrose seed oil | 8 | 43 | 65 | 24 | 700 |
| 7. Fatty acids of evening primrose seed oil (enriched fraction of Ex. 6*) | 68.3 | 37 | 65 | 18.8 | 700 |

| Examples starting material S.M. | Exchanger 2 Entry T. (°C.) | Exchanger 2 Exit T. (°C.) | Rotational speed of scraper (r.p.m.) | Exchanger 3 Entry T. (°C.) | Exchanger 3 Exit T. (°C.) | % GLA in enriched fraction | Yield (%) |
|---|---|---|---|---|---|---|---|
| 2. Fatty acids of blackcurrant seed oil | 30.1 | 9.9 | 1000 | 9.9 | 5.7 | 74.8 | 12.5 |
| 3. Fatty acids of blackcurrant seed oil | 17.6 | 6.3 | 1000 | — | — | 71.9 | 13.3 |
| 4. Fatty acids of comfrey seed oil | 16.5 | 5.5 | 100 | — | — | 94.2 | 16.5 |
| 5. Fatty acids of borage seed oil | 19 | 9 | 1000 | 10 | 3.9 | 94 | 15 |
| 6. Fatty acids of evening primrose seed oil | 23.9 | 12 | 1000 | 12 | 5.6 | 68.3 | 9 |
| 7. Fatty acids of evening primrose seed oil (enriched fraction of Ex. 6*) | 18.8 | 8.7 | 1000 | 8.7 | 3.5 | 93.8 | 45 |

— not determined
*In this case, the starting mixture is an enriched fraction treated a second time.

EXAMPLE 8

The procedure of Examples 2 to 7 is applied to the fractionation of the fatty acids of fish oil using a line of three scraped-surface heat exchangers of the VOTATOR type cooled with ice water to 1° C.

Fish oil does not contain any γ-linolenic acid, but other biologically active fatty acids, such as eicosapentaenoic acid $C_{20}:5$ and docosahexaenoic acid $C_{22}:6$.

The treatment conditions are shown in Table 2 below:

TABLE 2

| | Exchanger 1 | | | Exchanger 2 | | |
|---|---|---|---|---|---|---|
| Throughput (kg/h) | Entry T. (°C.) | Exit T. (°C.) | Rotational speed (r.p.m.) | Entry T. (°C.) | Exit T. (°C.) | Rotational speed (r.p.m.) |
| 49 | 65 | 37.3 | 700 | 37.2 | 23.7 | 1000 |

| Exchanger 3 | | | |
|---|---|---|---|
| Entry T. (°C.) | Exit T. (°C.) | Rotational Speed (r.p.m.) | Yield (%) |
| 23.7 | 8.9 | 500 | 18.9 |

The compositions of the fatty acids of the starting mixture and of the enriched fraction are shown in Table 3 below (determined by gas chromatography):

TABLE 3

| | Composition of the fatty acids (%) | | | |
|---|---|---|---|---|
| | $C_{18}:4$ | $C_{20}:5$ | $C_{22}:6$ | others |
| Starting material | 1.7 | 13.9 | 13.6 | 70.8 |
| Enriched fraction | 8.8 | 40.4 | 37.3 | 13.5 |

EXAMPLE 9

The procedure of Example 1 is applied to the fractionation of the fatty acids of linseed oil using a scraped-surface heat exchanger of the VOTATOR type cooled with ice water to 1° C.

The percentages of α-linolenic acid (α-LA) in the starting material and in the enriched fraction (determined by gas chromatography) and the parameters of the process are shown in Table 4 below:

TABLE 4

| | | Exchanger | | | | |
|---|---|---|---|---|---|---|
| % α-LA in the start-material | Through-put (kg/h) | Entry T. (°C.) | Exit T. (°C.) | Rotational speed (r.p.m.) | % α-LA in enriched fraction | Yield (%) |
| 54.5 | 66 | 40 | 16.6 | 700 | 87.6 | 18.1 |

EXAMPLE 10

The procedure of Example 1 is applied to the fractionation of a mixture of fatty acids emanating from lipids extracted from the placenta of mammals. This mixture contains a high percentage of arachidonic acid $C_{20}:4$ (AA) and dihomo-γ-linolenic acid $C_{20}:3$ (DHGLA). A scraped-surface heat exchanger of the VOTATOR type cooled with ethanol to $-16°$ C. is used.

The treatment conditions are shown in Table 5 below:

TABLE 5

| | Exchanger | | | |
|---|---|---|---|---|
| Throughput (kg/h) | Entry T. (°C.) | Exit T. (°C.) | Rotational speed (r.p.m.) | Yield (%) |
| 28 | 40 | 4 | 900 | 7 |

The percentages of the principal polyunsaturated fatty acids of the starting material and of the enriched fraction (determined by gas chromatography) are shown in Table 6 below.

TABLE 6

| Fatty acids | Starting material (%) | Enriched fraction (%) |
|---|---|---|
| $C_{18}:2$ | 12.2 | 17.8 |
| $C_{20}:3$ (DHGLA) | 5.1 | 9.6 |
| $C_{20}:4$ (AA) | 18 | 35.7 |
| $C_{22}:6$ | 8.2 | 17.4 |
| Others | 56.5 | 19.5 |

EXAMPLE 11

The procedure of Example 1 is applied to the fractionation of a mixture of fatty acids emanating from quandong seed oil. This mixture is characterized by contents of acetylenic acids, more especially santalbic acid or trans-11-octadecen-9-ynoic acid.

A scraped-surface heat exchanger of the VOTATOR type cooled with ethanol to $-16°$ C. is used. The treatment conditions and the percentages of santalbic acid of the starting material and of the enriched fraction (determined by gas chromatography) are shown in Table 7 below.

TABLE 7

| | | Exchanger | | | | |
|---|---|---|---|---|---|---|
| % Santalbic acid in starting material | Through-put (kg/h) | Entry T. (°C.) | Exit T. (°C.) | Rotational speed (r.p.m.) | % Santalbic acid in en-riched fraction | Yield (%) |
| 38.8 | 40 | 45 | 10 | 800 | 87.6 | 9 |

EXAMPLES 12-13

12.

Blackcurrant seed oil is fractionated in the same way as in Example 2, except that the liquid phase is separated from the solid phase by centrifugation for 10 minutes at 5000 r.p.m./4° C. instead of filtration. The fraction obtained contains 74% of GLA (determined by gas chromatography).

13.

Blackcurrant seed oil is fractionated in the same way as in Example 2, except that the fatty acids present in the solid phase are recovered. To this end, 1 part of the solid phase is heated to 80° C. with 2 parts water, 0.6 part hexane is added, the mixture is stirred and the organic phase is separated. The hexane is evaporated from the organic phase at 40° C. in a water pump vacuum. The fatty acids thus recovered are then added to the same quantity of untreated fatty acids.

The fractionation gives a mixture containing 67% of GLA (determined by gas chromatography) in a yield of 12.5%. The same quantity of GLA from approximately 25% less of fresh fatty acids is thus obtained.

We claim:

1. A process for fractionating a mixture of fatty acids, including derivatives thereof, containing polyunsaturated fatty acids, including derivatives thereof, for obtaining a fraction enriched with the polyunsaturated fatty acids, including derivatives thereof, comprising reacting a material selected from the group of materials consisting of a mixture of fatty acids and a mixture of fatty acids and derivatives thereof which contain polyunsaturated fatty acids, including derivatives thereof, with urea in solution for forming a reaction medium and then pumping the reaction medium to and through at least one and up to five scraped-surface heat exchangers for cooling the reaction medium for forming a dispersion of a solid inclusion complex and a liquid phase and then separating the liquid phase from the inclusion complex to obtain the liquid phase.

2. A process according to claim 1 wherein scraping elements of the heat exchangers rotate at a speed of from about 500 RPM to 3000 RPM.

3. A process according to claim 1 or 2 wherein the reaction medium is cooled by the at least one and up to five heat exchangers to a temperature of from −5° C. to 15° C.

4. A process according to claim 3 wherein the reaction medium to be pumped has a temperature of from 20° C. to 65° C.

5. A process according to claim 1 or 2 further comprising, after forming the reaction medium, cooling the reaction medium to a temperature of from 20° C. to 40° C. prior to pumping and wherein the reaction medium is cooled by the at least one and up to five heat exchangers to a temperature of from −5° C. to 15° C.

6. A process according to claim 1 or 2 further comprising directing the cooled dispersion from the at least one and up to five scraped-surface heat exchangers to a tank cooled to approximately 2° C. and then separating the liquid phase from the inclusion complex.

7. A process according to claim 3 further comprising directing the cooled dispersion from the at least one and up to five heat exchangers to a tank cooled to approximately 2° C. and then separating the liquid phase from the inclusion complex.

8. A process according to claim 2 wherein there is at least one and up to four scraped-surface heat exchangers and further comprising pumping the cooled dispersion from the at least one and up to four scraped surface heat exchangers to and through a dwell pipe provided with cooling means prior to separating the liquid phase from the inclusion complex.

9. A process according to claim 8 further comprising, after forming the reaction medium, cooling the reaction medium to a temperature of from 20° C. to 40° C. prior to pumping and wherein the reaction medium is cooled by the at least one and up to four heat exchangers and dwell pipe to a temperature of from −5° C. to 15° C.

10. A process according to claim 8 or 9 further comprising directing the cooled dispersion from the dwell pipe to a tank cooled to approximately 2° C. and then separating the liquid phase from the inclusion complex.

11. A process according to claim 1 further comprising adding water to the separated inclusion complex, heating the water and inclusion complex for releasing fatty acids and adding the released fatty acids to the mixture to be reacted with urea.

12. A process according to claim 1 wherein the urea is in a methanol solution.

13. A process according to claim 1 wherein the material to be reacted with urea is obtained from an oil obtained from seeds of the fruit of the genus Ribes.

14. A process according to claim 13 wherein the oil is obtained from seed of the fruit of *Ribes nigrum*.

15. A process according to claim 1 wherein the material to be reacted with urea is obtained from a fat substance selected from a group of fat substances consisting of linseed oil, comfrey oil, evening primrose seed oil, borage seed oil, quandong seed oil, fish oil, oil from crustaceans, oil from cephalopods, lipids emanating from organs of mammals and lipids emanating from body fluids of mammals.

* * * * *